(12) United States Patent
Dela

(10) Patent No.: US 10,172,701 B2
(45) Date of Patent: Jan. 8, 2019

(54) DOUBLE ENDED VASCULAR FILTER

(71) Applicant: COOK MEDICAL TECHNOLOGIES LLC, Bloomington, IN (US)

(72) Inventor: Christian Dela, Valby (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 212 days.

(21) Appl. No.: 15/015,534

(22) Filed: Feb. 4, 2016

(65) Prior Publication Data
US 2016/0220344 A1    Aug. 4, 2016

(30) Foreign Application Priority Data

Feb. 4, 2015 (GB) .................................. 1501849.2

(51) Int. Cl.
  *A61F 2/01*    (2006.01)
  *A61B 17/12*   (2006.01)

(52) U.S. Cl.
  CPC .......... *A61F 2/01* (2013.01); *A61B 17/12172* (2013.01); *A61F 2/013* (2013.01); *A61F 2002/016* (2013.01); *A61F 2230/0004* (2013.01); *A61F 2230/0006* (2013.01);
  (Continued)

(58) Field of Classification Search
  CPC ...... A61F 2/01; A61F 2/013; A61F 2002/016; A61F 2230/0004; A61F 2230/0006; A61F 2230/0008; A61F 2230/0067; A61F 2230/0091; A61B 17/12172
  See application file for complete search history.

(56) References Cited

U.S. PATENT DOCUMENTS

| 4,494,531 A | 1/1985  | Gianturco     |
|-------------|---------|---------------|
| 5,370,657 A | 12/1994 | Irie          |
| 6,059,825 A | 5/2000  | Hobbs et al.  |

(Continued)

FOREIGN PATENT DOCUMENTS

| DE | 4339265 | 5/1995  |
|----|---------|---------|
| EP | 1987800 | 11/2008 |

(Continued)

OTHER PUBLICATIONS

Examination Report for GB1501849.2, dated May 31, 2016.

*Primary Examiner* — Robert Lynch
(74) *Attorney, Agent, or Firm* — Brinks Gilson & Lione

(57) ABSTRACT

An implantable vascular filter includes an elongate support element, a first flexible filtering element, a first coupling element at or proximate a first end of the support element for coupling to a retrieval device, and a second coupling element at or proximate a second end of the support element for coupling to a retrieval device. The first flexible filtering element has a first end attached to the support element and a second end movable with respect to the support element and is able to be configured into any of a radially expanded filtering configuration, a first collapsed configuration, and a second collapsed configuration. The first filtering element is biased into the filtering configuration when in a deployed condition, and is collapsible from the filtering configuration into either of the first collapsed configuration or the second collapsed configuration.

22 Claims, 1 Drawing Sheet

(52) U.S. Cl.
CPC ............. *A61F 2230/0008* (2013.01); *A61F 2230/0067* (2013.01); *A61F 2230/0091* (2013.01)

(56) References Cited

U.S. PATENT DOCUMENTS

| | | |
|---|---|---|
| 6,063,113 A | 5/2000 | Kavteladze et al. |
| 8,062,328 B2 | 11/2011 | Hallisey |
| 2001/0031980 A1 | 10/2001 | Wensel et al. |
| 2002/0151966 A1 | 10/2002 | Eder et al. |
| 2002/0193825 A1 | 12/2002 | McGuckin, Jr. et al. |
| 2003/0040771 A1 | 2/2003 | Hyodoh et al. |
| 2004/0186512 A1 | 9/2004 | Bruckheimer et al. |
| 2007/0239199 A1 | 10/2007 | Jayaraman |
| 2008/0275496 A1* | 11/2008 | Fleming ............... A61F 2/01 606/200 |
| 2010/0063533 A1 | 3/2010 | Sokolov et al. |
| 2011/0106134 A1* | 5/2011 | Thompson ............ A61F 2/013 606/200 |

FOREIGN PATENT DOCUMENTS

| | | |
|---|---|---|
| WO | WO 1995/013761 | 5/1995 |
| WO | WO 2005/117750 | 12/2005 |
| WO | WO 2007/133366 | 11/2007 |
| WO | WO 2010/091118 | 8/2010 |

* cited by examiner

DOUBLE ENDED VASCULAR FILTER

CROSS-REFERENCE TO RELATED APPLICATIONS

This application claims the benefit of priority under 35 U.S.C. § 119(a) to Great Britain Patent Application No. GB 1501849.2, filed Feb. 4, 2015, which is hereby incorporated by reference in its entirety.

TECHNICAL FIELD

The present invention relates to vascular filters, for example filters suitable for deployment in the inferior vena cava.

BACKGROUND ART

Vena cava filters are often deployed in a patient's vessel, left in position for a period during which filtration is deemed necessary and then removed from the patient.

It is typical to deploy filters via the femoral or jugular into the vena cava. On the other hand, as a result of their shape and the retrieval geometry, the withdrawal of filters from the patient's vasculature is normally carried out from the jugular side. Such retrieval can involve the formation of a second percutaneous entry into the patient.

Attempts have been made to provide a filter which is removable from either the femoral or the jugular side.

Examples of known filters include WO 2005/117750, WO 95/13761, WO 2010/091118, U.S. Pat. No. 8,062,328, US2003/0040771, US2010/0063533, US2004/0186512, US2003/0040771, U.S Pat. Nos. 4,494,531, 6,059,825, US2007/0239199, US2002/0193825, U.S. Pat. No. 6,063,113.

DISCLOSURE OF THE INVENTION

The present invention seeks to provide an improved vascular filter.

According to an aspect of the invention, there is provided an implantable vascular filter, including:

an elongate support element having a longitudinal axis;

a first flexible filtering element having a first end attached to the support element and a second end movable with respect to the support element, the first filtering element being able to be configured into any of a radially expanded filtering configuration, a first collapsed configuration in which the whole of the first filtering element is collapsed in a first longitudinal direction, and a second collapsed configuration in which the whole of the first filtering element is collapsed in a second longitudinal direction opposite to the first longitudinal direction; the first filtering element being biased into the filtering configuration when in a deployed condition, and being collapsible from the filtering configuration into either of the first collapsed configuration or the second collapsed configuration;

a first coupling element at or proximate a first end of the support element for coupling to a retrieval device; and a second coupling element at or proximate a second end of the support element for coupling to a retrieval device;

wherein the first filtering element includes a coil.

Embodiments of the invention provide a filter that can be completely collapsed in either of two longitudinal directions, allowing the filter to be conveniently removed from either direction. This can mean that the filter when deployed in the inferior vena cava, can be retrieved from either a femoral or jugular approach.

The presence of an elongate support element to which are attached the first and second coupling elements and the first filtering element means that in embodiments the filter can be snared more easily by a retrieval device since the elongate support element will tend to remain substantially central within a vessel. In addition, the support element provides a support for the radial expansion of the first filtering element, enabling it to expand with a greater force than is possible for a single unsupported wire. This can mean that the first filtering element can secure itself more reliably to the wall of the vessel into which it is implanted, while still being capable of retrieval from either direction.

Preferably the second end of the first filtering element is free from attachment to the support element.

Preferably in the filtering configuration, the first filtering element has a radial size which increases from the first end to the second end, enabling the first filtering element to adopt an advantageous filtering shape.

Preferred embodiments include a second flexible filtering element having a first end movable with respect to the support element and a second end attached to the support element; the second filtering element being able to be configured into any of a radially expanded filtering configuration, a first collapsed configuration in which the whole of the second filtering element is collapsed in the first longitudinal direction, and a second collapsed configuration in which the whole of the second filtering element is collapsed in the second longitudinal direction; the second filtering element being biased into the filtering configuration when in a deployed condition, and being collapsible from the filtering configuration into either of the first collapsed configuration or the second collapsed configuration.

Having two filtering elements can mean that the filtering arrangement as a whole is made longer, thereby improving the filtering action. Single wires, if they are to be retrievable, have a practical limit on their length if they are likely to be susceptible to ingrowth. Ingrowth on a long single wire can make retrieval difficult. However, by having a plurality of wires, embodiments of the present invention can provide a greater overall length without this problem. The dual direction retrievability is facilitated since both filtering elements are attached to the elongate support element which is used for retrieval.

Preferably, the first end of the second filtering element is free from attachment to the support element.

Preferably, in the filtering configuration, the second filtering element has a radial size which increases from the second end to the first end.

Preferably, the first and second flexible filtering elements are in the filtering configurations arranged in a confronting configuration. In embodiments, the filtering elements can be transitioned from the filtering configurations to either of the collapsed configurations by being drawn into a sheath. The confronting configuration can assist, in such embodiments, in facilitating the withdrawal process in either direction.

Preferably, the first and second flexible filtering elements are distinct and separate elements and are preferably longitudinally separated in the filtering configurations. This can prevent the filtering elements from becoming tangled.

In embodiments, a first end of the first filtering element is attached to the support element adjacent to the first end of the support element and the second end of the second filtering element is attached to the support element adjacent to a second end of the support element.

In embodiments, the first and second filtering elements have opposing tapers. In other words, the radial sizes of the first and second filtering elements taper in opposite directions, meaning that the first and second filtering elements could be said to have opposing widening forms.

In embodiments, the first and second filtering elements are coils, for example coiled wires, that coil in opposite senses, that is to say that when looking along the elongate support element in a longitudinal direction, one of the filtering elements will coil in a clockwise sense, and the other in an anticlockwise sense.

The filtering elements can in their filtering configurations be symmetrical with respect to each other. In some embodiments, the filtering elements can in the filtering configuration be conical or can form an oval shape in which the major axis can be longitudinal or transverse.

Preferably, in the filtering configuration the filtering element or filtering elements form a symmetrical shape, which is preferably substantially spherical.

In embodiments, the first and/or second filtering element includes a coil.

In embodiments, the first and/or second filtering element includes a wire.

In embodiments, the support element is unitary such as an integral unitary structure.

The first and/or second filtering element can include shape memory material and/or spring material whereby when in a deployed condition it is or they are biased into the filtering configuration.

In embodiments, the first and second coupling elements are for selectively coupling to a retrieval device.

In embodiments, the filter includes two Nitinol wires, both with a semisphere shape, memory shaped to take up sphere shape when deployed. The sphere shape includes two wires mounted on a centre backbone with hooks in each end. The Nitinol wire grows into the cava, but retrieval is easy. The wire simply slides through and out from the overgrowth. The wires elongate to a straight line during retrieval.

Also described herein is a method of retrieving an implantable vascular filter from a vessel, the filter including:
 a elongate support element having a longitudinal axis;
 a first flexible filtering element having a first end attached to the support element and a second end movable with respect to the support element, the first filtering element being able to be configured into any of a radially expanded filtering configuration, a first collapsed configuration in which the whole of the first filtering element is collapsed in a first longitudinal direction, and a second collapsed configuration in which the whole of the first filtering element is collapsed in a second longitudinal direction opposite to the first longitudinal direction; the first filtering element being biased into the filtering configuration when in a deployed condition, and being collapsible from the filtering configuration into either of the first collapsed configuration or the second collapsed configuration;
 a first coupling element at or proximate a first end of the support element for coupling to a retrieval device; and
 a second coupling element at or proximate a second end of the support element for coupling to a retrieval device;
 the method including the steps of:
 advancing a retrieval assembly to a site where the filter is located, wherein the retrieval assembly includes a retrieval sheath and a third coupling element;
 coupling the third coupling element to the first or second coupling element of the filter;
 applying a retrieval force to the third coupling element to draw the filter into the retrieval sheath, wherein drawing the filter into the retrieval sheath causes the first filtering element to be collapsed into either the first or second collapsed configuration;
 withdrawing the retrieval sheath including the filter from the patient.

In preferred embodiments, the filter includes first and second filtering elements as described above and drawing the device into the retrieval sheath causes both the first and the second filtering elements to be collapsed into their first collapsed configurations, or into their second collapsed configurations.

The third coupling element can include a snare, for example mounted on a snare catheter.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Described below are preferred embodiments of the device taught herein. It is to be understood that the drawings are not to scale and are intended to be merely illustrative of the features and elements of the device and its components taught herein.

References to the shape and/or arrangement of the filter in the filtering configuration are primarily references to the shape and/or arrangement in a rest condition of the filtering configuration. Such features of the shape and/or arrangement may also be present when implanted in a vessel, but may be affected by the shape and configuration of the vessel.

Throughout this specification the term proximal with respect with both human or animal vasculature will be used to refer to the region closest to the heart and similarly that part of the implantable medical device which when in use is closest to the heart, while the term distal will be used for the regions of the human or animal vasculature further from the heart and similarly those parts of the implantable medical device which in use are further from the heart. With regard to a deployment or introducer assembly or retrieval device, the term distal is also used to denote the part of the assembly which remains closest to the clinician during the medical procedure, and typically outside the patient, and the term proximal is also used to denote the end of the assembly which is furthest from the clinician and which is first fed endoluminally into the patient's vasculature.

Figure 1:
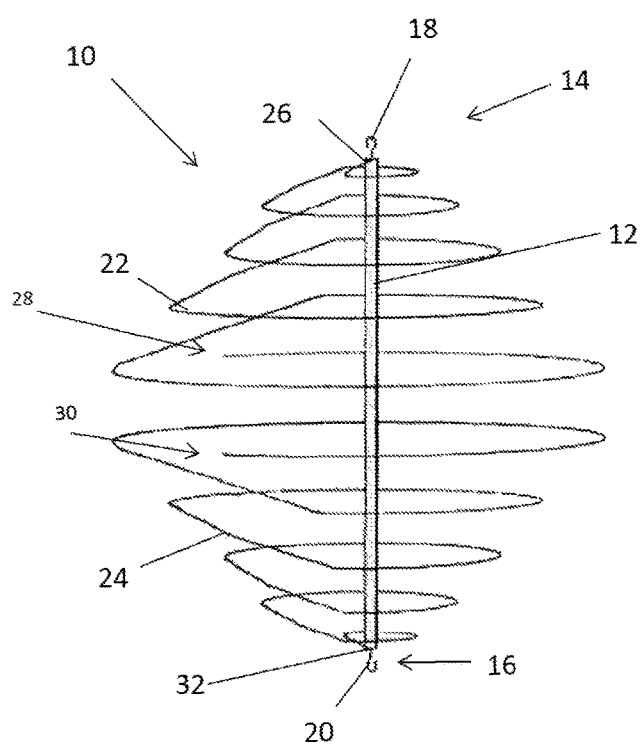
FIG. 1 is a schematic diagram of an implantable medical device in a filtering configuration according to an embodiment of the invention.

Referring first to FIG. 1, there is shown in schematic form an implantable vascular filter 10 in a filtering configuration. The filter 10 includes an elongate support element 12 having a longitudinal axis. The elongate support element 12 could be described as providing a backbone to the device. Various components can be used to provide the support element 12. However, in some embodiments it is provided by a steel body such as a cannula but in other embodiments it can be a flexible structure including a polymer such as is typically used for a catheter sheath; in such embodiments it may include a strengthening coil.

The support element includes a proximal end 14 and a distal end 16. At the proximal end 14 of the elongate support element, there is provided a first coupling element 18 which is configured for coupling to a retrieval device 42. Various forms of coupling elements can be provided. In the preferred embodiment, the coupling element 18 is a hook for being snared by a retrieval snare.

At the distal end 16 of the support element 12 there is provided a second coupling element 20 which is configured for coupling to a retrieval device 42. The second coupling element 20 can be similar to or different from the coupling element 18. In the preferred embodiment, coupling elements 18 and 20 are similar so that a retrieval device can be selectively coupled to either the first or second coupling element.

The filter 10 includes a first flexible filtering element 22 and a second flexible filtering element 24. The first flexible filtering element 22 is attached to and fixed with respect to the proximal end 14 of the elongate support element 12 at a first end 26 of the first filtering element 22. The second end 28 of the first filtering element 22 is unattached, that is free from attachment, and movable with respect to the support element 12.

Correspondingly, the second filtering element 24 includes a first end 30 which is unattached, that is free from attachment, and movable with respect to the support element 12, and a second end 32 which is attached to the distal end of the support element 12 in such a way that the second end 32 of the second filtering element 24 is fixed with respect to the support element 12.

Each of the first and second filtering elements can be configured into any of a radially expanded filtering configuration, a first collapsed configuration in which the whole of the respective filtering element is collapsed in a first longitudinal direction, and a second collapsed configuration in which the whole of the respective filtering element is collapsed in a second longitudinal direction opposite to the first longitudinal direction. In the depicted embodiment, the first longitudinal direction is a distal direction and the second longitudinal direction is a proximal direction, however they could equally be the other way round.

The first and second filtering elements are configured so that in the radially expanded filtering configurations they permit the flow of blood but capture larger elements passing in the bloodstream such as emboli, or at least prevent or restrict their flow. In the depicted embodiment, each of the first and second filtering elements includes a single wire which in the filtering configuration coils around the longitudinal axis of the elongate support element 12 forming a series of loops or a coil. The coil of the first filtering element extends from the proximal end 14 of the support element 12 towards the centre of the support element and the coil of the second filtering element extends from the distal end of the support element towards the centre of the support element. The coil of the first filtering element has a gradually increasing radial size from the first end to the second end so that more central loops of the coil have a greater diameter than less central loops. Similarly, the coil of the second filtering element has a gradually increasing size from the second end to the first end so that more central loops have a greater diameter than the less central loops. The coils of the first and second filtering elements coil around the support element in opposite senses. Looking along the support element from the distal end to the proximal end, the first filtering element coils in a clockwise sense while the second filtering element coils in an anticlockwise sense.

The wire of each of the first and second filtering elements has a length substantially equal to a length of the support element so that each of the first and second filtering elements can be straightened to a form in which it is substantially coextensive with the support element. However, this is not necessary in every embodiment.

In the depicted embodiment, each filtering element has 5 loops, however, there can in other embodiments be more or fewer loops.

In the depicted embodiment, the loops have a constant density. However, in other embodiments, the loops of the first filtering element can be denser in a proximal region than in a distal region and the loops of the second filtering element can be denser in a distal region than in a proximal region.

Each of the filtering elements 22, 24 in the filtering configuration forms a substantially hemispherical shape with what could be described as an apex at the end of the filtering element which is attached to the elongate support element 12 and with a base at the free end of the filtering element so that the base is movable with respect to the support element 12.

The first and second filtering elements are arranged in a confronting configuration as shown in FIG. 1 so that together they form a substantially spherical filtering arrangement. In this embodiment, each filtering element has an inverse taper from a smaller transverse cross-section near its attached end to a greater transverse cross-section near its free end.

However, the filtering elements do not need to be substantially hemispherical in all embodiments. For example, the filtering elements can be coiled in a conical arrangement. Furthermore, in some embodiments each of the filtering elements can in the filtering configuration have a non-circular cross-section, such as an oval cross-section. In the filtering configuration, the filtering elements preferably form a substantially symmetrical shape which is symmetrical about a midpoint between the points of attachment to the support element. However, this is not necessary in all embodiments as the filtering elements can form an egg shape in some embodiments.

The filter 10 can easily be removed from an implant site from either its proximal or its distal end.

The first and second filtering elements 22, 24 are biased into the filtering configuration. This can be achieved for example by each of the filtering elements 22, 24 being made of or including a shape memory material such as Nitinol. However, it can also be achieved by other biasing means, for example by the filtering elements 22, 24 being made of or including spring steel.

In other words, the filter includes the elongate support element 12; the first filtering element 22, the first end of which is attached to the proximal end of the support element 12; and the second filtering element 24, the second end of which is attached to the distal end of the support element 12. The first and second filtering elements are single coiled wires which coil towards each other, from opposite ends of the support element, in opposite senses, and with increasing displacement from the support element, thereby to form coils which increase in radial size towards each other so as to provide opposing widening forms which are symmetrical with respect to each other. Looking along the support element 12 from the distal end to the proximal end, the first filtering element coils in a clockwise sense and the second filtering element coils in an anticlockwise sense. Each of the first and second filtering elements forms a shape which increases in radial size from a first end of the shape at its point of attachment to the support element 12 towards the centre of the support element 12 to a region of maximum radius and a second end of the shape where the filtering elements have a free end free from attachment to the support element 12. The diameters of the wires of the first and second filtering elements are typically constant.

As described above, each of the first and second filtering elements is able to be configured into a first collapsed configuration in which the whole of the respective filtering element is collapsed in a first longitudinal direction, and a second collapsed configuration in which the whole of the respective filtering element is collapsed in a second longitudinal direction opposite to the first longitudinal direction.

Figure 2:
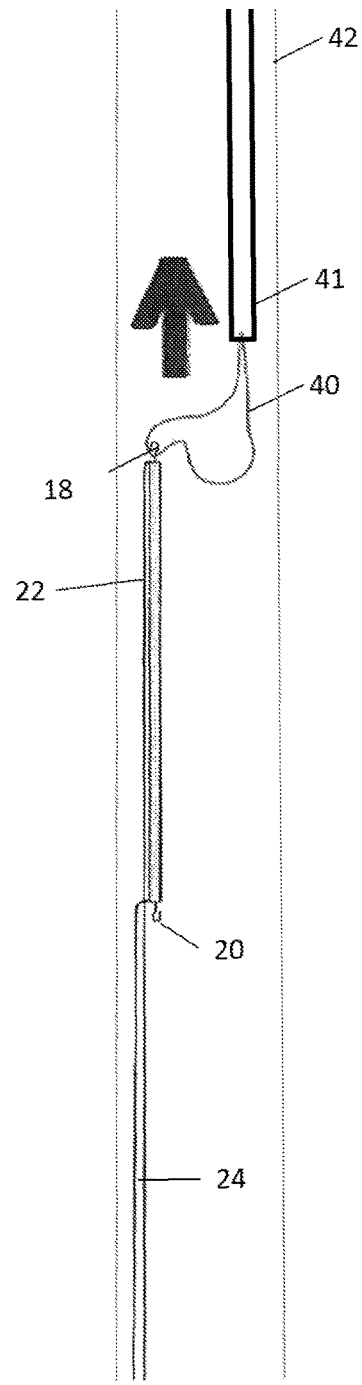
FIG. 2 is a schematic diagram of the implantable medical device of FIG. 1 in a collapsed configuration.

FIG. 2 shows a first collapsed configuration in which the first and second filtering elements are compressed into a substantially straight longitudinal configuration. In this configuration, both filtering elements extend in a substantially straight line distally from their point of attachment to the support element 12. The transverse cross-section of the filter is therefore substantially the same as the transverse cross-section of the support element. It will be noted from FIG. 2 that the second filtering element in this configuration extends distally of the distal end of the support element. The second collapsed configuration has a corresponding arrangement but both filtering elements extend proximally from their point of attachment to the support element.

In order to deploy a filter in a patient, the device is placed in a collapsed configuration inside a sheath in an introducer assembly and advanced to the filtering site. Then the sheath is withdrawn from the filter. As the sheath is withdrawn, the filtering elements 22, 24, as a result of their being biased into the filtering configuration, radially expand to the filtering configuration. Since the filtering elements are mounted onto an elongate support element backbone, this support element is able to provide a strong support enabling the filtering elements to provide a strong expansion force into the filtering configuration, thereby assisting their deployment and achieving a secure hold within the vessel in which they need to provide a filtering function.

When it is desired to retrieve the filter, a retrieval apparatus can be advanced to either the proximal or distal end of the filter 10.

A snare catheter 41 to which is coupled a snare 40 can be advanced to the filtering site inside a retrieval sheath 42. When in the vicinity of the filtering site, the snare catheter 41 can be advanced so that the snare 40 exits the retrieval sheath. The snare 40 is used to snare either the first or second coupling elements 18, 20 by being passed over and caught by the hook. In FIG. 2 the snare is shown having snared the first coupling element 18 but the retrieval apparatus could equally be advanced from the opposite direction and the snare used to snare the second coupling element 20.

Once the snare 40 has snared the appropriate element, the snare catheter 41 is retracted thereby to cause the snare 40 to draw the filter into the retrieval sheath 42.

Where the first coupling element 18 is snared, when the filter is drawn into the sheath the first filtering element will come into contact with the sheath and the sheath will provide a distal force against it. This force will cause the first filtering element 22 to collapse and straighten in order to fit within the sheath. As the first filtering element 22 collapses and straightens, its longitudinal length increases.

Once the sheath has reached the distal end of the support element 12, the first filtering element 22 is substantially straight and compressed against the support element in the first collapsed configuration.

As the distal end of the support element 12 is drawn into the sheath, the sheath begins to extend and compress the second filtering element 24, pushing it into an elongated straight longitudinal configuration in a corresponding manner. Eventually, the filter 10 will have adopted the configuration shown in FIG. 2 in which the first filtering element 22 lies substantially straight against the support element 22, and the second filtering element lies substantially straight beyond the distal end of the support element 22, both filtering elements being within the sheath. This provides a very thin configuration for easy retrieval.

The filter can then conveniently be removed from the vasculature.

Although compression into the first collapsed configuration is described above, the filter 10 can alternatively be retrieved the other way round in which the second coupling element 20 is snared and the distal end 16 of the filter is first drawn into the sheath, thereby compressing the second filtering element 24 against the support element 12 and extending the first filtering element 22 beyond the proximal end of the support element 12 to put the filtering elements into the second collapsed configuration. This process operates in an analogous manner to that described above for compression into the first collapsed configuration.

Although the embodiments described above include first and second filtering elements, it is possible to provide a filter including only one of the filtering elements described above. However, a single filtering element has limits on its length if it is to be easily retrievable since ingrowth can occur and this can make it more difficult to retrieve a long filtering element. Providing first and second filtering elements is able to provide additional length without overly restricting the ability of the filtering elements to be detached from the vessel wall.

In addition, although in the embodiments described above the filtering elements are longitudinally separated and provided in a confronting configuration, this is not necessary in all embodiments. The filtering elements can be intermeshed and/or arranged in any desired suitable filtering configuration. However, the separated confronting configuration of the preferred embodiment is advantageous because it reduces the likelihood for the filtering elements to become ensnared with each other.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. An implantable vascular filter, comprising an elongate support element having a longitudinal axis;
   a first flexible filtering element the first filtering element including a coil and having a first end attached to the support element and a second end movable with respect to the support element, the first filtering element being able-to be configured into any of a radially expanded filtering configuration, a first collapsed configuration in which the whole of the first filtering element is collapsed in a first longitudinal direction, and a second collapsed configuration in which the whole of the first filtering element is collapsed in a second longitudinal direction opposite to the first longitudinal direction; the first filtering element being biased into the filtering configuration when in a deployed condition, and being collapsible from the filtering configuration into either of the first collapsed configuration or the second collapsed configuration;
   a first coupling element at or proximate a first end of the support element for coupling to a retrieval device; and a second coupling element at or proximate a second end of the support element for coupling to a retrieval device;

a second flexible filtering element having a first end movable with respect to the support element and a second end attached to the support element; the second filtering element being able to be configured into any of a radially expanded filtering configuration, a first collapsed configuration in which the whole of the second filtering element is collapsed in the first longitudinal direction, and a second collapsed configuration in which the whole of the second filtering element is collapsed in the second longitudinal direction; the second filtering element being biased into the filtering configuration when in a deployed condition, and being collapsible from the filtering configuration into either of the first collapsed configuration or the second collapsed configuration;

wherein the second filtering element includes a coil;

wherein the filter includes a first retrieval condition in which both the first and second filtering elements are collapsed into the first collapsed configuration and the whole of the first filtering element extends from its first end to its second end in the first longitudinal direction and the whole of the second filtering element extends from its second end to its first end in the first longitudinal direction, wherein the first retrieval condition is in response to retrieval in the second longitudinal direction; and wherein the filter includes a second retrieval condition in which both the first and second filtering elements are collapsed into the second collapsed configuration and the whole of the first filtering element extends from its first end to its second end in the second longitudinal direction and the whole of the second filtering element extends from its second end to its first end in the second longitudinal direction, wherein the second retrieval condition is in response to retrieval in the first longitudinal direction.

2. The filter according to claim 1, wherein the second end of the first filtering element is free from attachment to the support element.

3. The filter according to claim 1, wherein in the filtering configuration the first filtering element has a radial size which increases from the first end to the second end.

4. The filter according to claim 1, wherein the first end of the second filtering element is free from attachment to the support element.

5. The filter according to claim 1, wherein in the filtering configuration the second filtering element has a radial size which increases from the second end to the first end.

6. The filter according to claim 1, wherein the first and second flexible filtering elements are in their respective filtering configurations arranged in a confronting configuration.

7. The filter according to claim 1, wherein the first and second flexible filtering elements are distinct and separate elements.

8. The filter according to claim 1, wherein the first and second flexible filtering elements are longitudinally separated in their respective filtering configurations.

9. The filter according to claim 1, wherein the first end of the first filtering element is attached to the support element adjacent to a first end of the support element and the second end of the second filtering element is attached to the support element adjacent to a second end of the support element.

10. The filter according to claim 1, wherein in the respective filtering configurations the first and second filtering elements have opposing tapers.

11. The filter according to claim 1, wherein in the respective filtering configurations each of the first and second filtering elements includes a coil and the coils are coiled in opposite senses.

12. The filter according to claim 1, wherein in the respective filtering configurations the first end of the first filtering element is longitudinally displaced from the second end of the first filtering element in the first longitudinal direction and the second end of the second filtering element is longitudinally displaced from the first end of the second filtering element in the second longitudinal direction.

13. The filter according to claim 1, wherein in the filtering configuration the first and second filtering elements form a symmetrical shape.

14. The filter according to claim 13, wherein the symmetrical shape is substantially spherical.

15. The filter according to claim 1, wherein the first and second filtering element each include a wire.

16. The filter according to claim 15, wherein the first filtering element consists of a single wire biased to coil and the second filtering element consists of a single wire biased to coil.

17. The filter according to claim 1, wherein the support element is a unitary structure.

18. The filter according to claim 1, wherein in the filtering configuration the first filtering element has a region of smallest diameter at the first end of the first filtering element and in the filtering configuration the second filtering element has a region of smallest diameter at the second end of the second filtering element.

19. The filter according to claim 1, wherein for the first filtering element and for the second filtering element, the first end is longitudinally displaced from the second end in the filtering configuration.

20. The filter according to claim 1, wherein the first and second filtering element includes shape memory material and/or spring material whereby when in the deployed condition they are biased into the respective filtering configuration.

21. The filter according to claim 1, wherein in the first or second collapsed configuration, the first and second filtering element is substantially straight.

22. The filter according to claim 1, wherein in the first or second collapsed configuration, the first and second filtering element is substantially longitudinal.

* * * * *